United States Patent [19]

Theobald et al.

[11] 4,229,205

[45] Oct. 21, 1980

[54] SUBSTITUTED ALKOXYIMINO-PYRIDAZONES, THEIR MANUFACTURE, AND THEIR USE AS HERBICIDES

[75] Inventors: Hans Theobald; Bruno Wuerzer, both of Limburgerhof; Karl Kiehs, Lampertheim, all of Fed. Rep. of Germany

[73] Assignee: BASF Aktiengesellschaft, Fed. Rep. of Germany

[21] Appl. No.: 34,857

[22] Filed: Apr. 30, 1979

[30] Foreign Application Priority Data

May 19, 1978 [DE] Fed. Rep. of Germany ....... 2821809

[51] Int. Cl.$^2$ ..................... C07D 237/22; A01N 9/22
[52] U.S. Cl. ......................................... 71/92; 544/241
[58] Field of Search ..................... 544/239, 241; 71/92

[56] References Cited

U.S. PATENT DOCUMENTS

| 3,157,646 | 11/1964 | Reicheneder | 544/241 |
| 3,193,553 | 7/1965 | Reicheneder | 544/241 |
| 3,210,353 | 10/1965 | Reicheneder | 544/241 |
| 3,222,159 | 12/1965 | Reicheneder | 71/92 |

FOREIGN PATENT DOCUMENTS

| 1105232 | 12/1961 | Fed. Rep. of Germany . |
| 1123510 | 9/1962 | Fed. Rep. of Germany . |
| 1224981 | 9/1966 | Fed. Rep. of Germany ........... 544/241 |

Primary Examiner—Mark L. Berch
Attorney, Agent, or Firm—Keil & Witherspoon

[57] ABSTRACT

New pyridaz-6-ones having a good herbicidal action, herbicides containing these compounds, and a process for controlling unwanted plant growth with these compounds.

3 Claims, No Drawings

SUBSTITUTED ALKOXYIMINO-PYRIDAZONES, THEIR MANUFACTURE, AND THEIR USE AS HERBICIDES

The present invention relates to new and valuable pyridaz-6-ones having a good herbicidal action, herbicides containing these compounds, and a process for controlling unwanted plant growth with these compounds.

The use of 1-phenyl-4-dialkylaminopyridazones and 1-cyclohexyl-4-dialkylaminopyridazones as selective herbicides has been disclosed (German Pat. No. 1,105,232 and German Pat. No. 1,123,510).

We have found that pyridaz-6-one derivatives of the formula

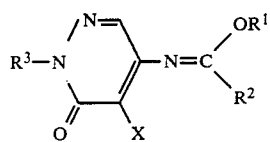

where X denotes halogen (Cl, Br), $R^1$ denotes $C_1$-$C_6$-alkyl ($CH_3$, $C_2H_5$), $R^2$ denotes H, $C_1$-$C_6$-alkyl ($CH_3$, $C_2H_5$) or haloalkyl (Cl—$CH_2$), and $R^3$ denotes phenyl or cyclohexyl, exhibit, both pre- and postemergence, a considerable herbicidal action, and do no harm to the crop plants.

The new compounds are prepared by reaction of o-carboxylic acid esters (III) with pyridazone derivatives (II) in the presence of acids, at from 80° to 200° C. The reaction takes place for instance in accordance with the following scheme

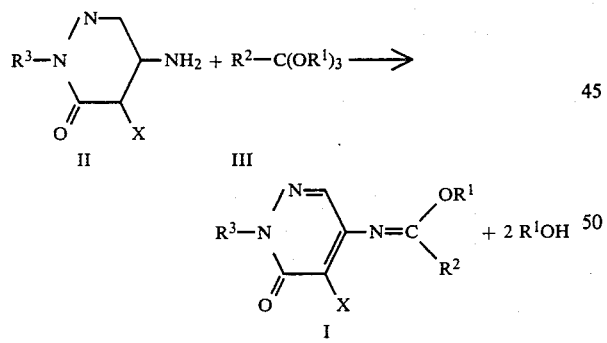

where X, $R^1$, $R^2$ and $R^3$ have the above meanings.

Examples of acids present during the reaction are phosphoric acid, sulfuric acid, hydrogen halides, organic sulfonic acids, and haloacetic acids. The alcohol $R^1OH$ formed during the reaction is distilled off from the reaction mixture. In the reaction of II and III to give I, equimolar amounts of II and III, but preferably an excess of III, are used. As solvent, III itself may be used, or all solvents which do not react with III, II or I and have a boiling point higher than $R^1OH$, e.g., benzene, toluene, and halobenzenes.

EXAMPLE 1

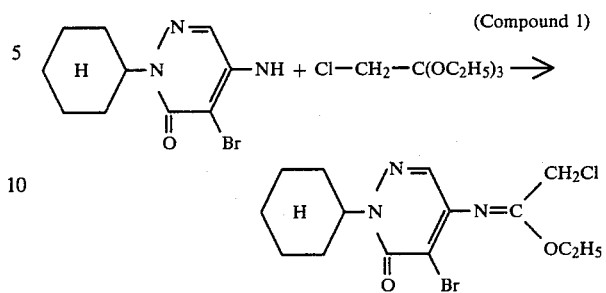

(Compound 1)

230 g of 1-cyclohexyl-5-bromo-4-aminopyridaz-6-one, 1 liter of triethyl o-chloroacetate, and 5 g of o-phosphoric acid were mixed, the mixture was heated to 130° C., and the ethyl alcohol liberated was distilled off from the reaction mixture. The reaction solution was then stirred for 1 hour at 150° C., cooled, and washed with 5% strength aqueous $Na_2CO_3$ solution and water; after drying over $Na_2SO_4$ the remaining solution was concentrated and the residue recrystallized from petroleum ether. There is obtained 273 g of compound 1; yield: 86%; m.p.: 74°-78° C.

| | | | | | |
|---|---|---|---|---|---|
| Calc. | C 44.6 | H 5.1 | N 11.2 | Cl 9.44 | Br 21.2 |
| Found | C 44.9 | H 5.2 | N 11.4 | Cl 8.9 | Br 21.0 |

If 1-phenyl-5-bromo-4-aminopyridaz-6-one is used instead of 1-cyclohexyl-5-bromo-4-aminopyridaz-6-one, the compound

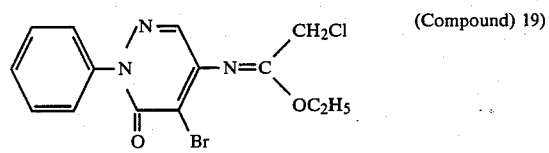

(Compound) 19)

is obtained analogously.

The following compounds were prepared analogously:

| Compound no. | X | $R^2$ | $R^1$ | $R^3$ | m.p.(°C.) |
|---|---|---|---|---|---|
| 2. | Br | H | $C_2H_5$ | $C_6H_{11}$ | 95–97 |
| 3. | Br | $CH_3$ | $CH_3$ | $C_6H_{11}$ | 100–101 |
| 4. | Br | $CH_3$ | $C_2H_5$ | $C_6H_{11}$ | 60 MHz NMR spectrum in $CDCl_3$ (δ values) 1.24 (3H); 1.84 (3H); 1.3–1.7 (10H); 4.02 (2H); 4.71 (1H); 7.19 (1H) |
| 5. | Br | $C_2H_5$ | $C_2H_5$ | $C_6H_{11}$ | 60 MHz spectrum in $CDCl_3$ (δ values) 1.01 (3H); 1.24 (3H); 1.3–1.82 (10H); 1.97 (2H); 4.13 (2H); 4.74 (1H); 7.22 (1H). |
| 6. | Br | H | $CH_3$ | $C_6H_{11}$ | 124–125 |
| 7. | Br | $CH_2Cl$ | $CH_3$ | $C_6H_{11}$ | 122–125 |
| 8. | Cl | $CH_3$ | $C_2H_5$ | $C_6H_{11}$ | 89–91 |
| 9. | Cl | $C_2H_5$ | $C_2H_5$ | $C_6H_{11}$ | 270 MHz NMR |

-continued

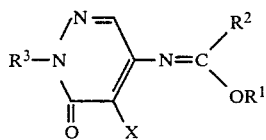

| Compound no. | X | R² | R¹ | R³ | m.p.(°C.) |
|---|---|---|---|---|---|
| | | | | | spectrum in CDCl₃ (δ values) 1.1 (3H); 1.28 (3H); 1.15-1.95 (10H); 2.2 (2H); 4.3 (2H); 4.95 (1H); 7.5 (1H) |
| 10. | Cl | H | CH₃ | C₆H₁₁ | 93 |
| 11. | Cl | CH₂Cl | C₂H₅ | C₆H₁₁ | 73-74 |
| 12. | Cl | H | C₂H₅ | C₆H₁₁ | 105-115 |
| 13. | Cl | H | C₂H₅ | C₆H₅ | 128-130 |
| 14. | Br | H | CH₃ | C₆H₅ | 85-88 |
| 15. | Br | H | C₂H₅ | C₆H₅ | 113-114 |
| 16. | Br | CH₃ | CH₃ | C₆H₅ | 98-100 |
| 17. | Br | CH₃ | C₂H₅ | C₆H₅ | 57-60 |
| 18. | Br | C₂H₅ | C₂H₅ | C₆H₅ | 78-80 |
| 19. | Br | CH₂Cl | C₂H₅ | C₆H₅ | 80-81 |
| 20. | Cl | CH₃ | C₂H₅ | C₆H₅ | |
| 21. | Cl | H | CH₃ | C₆H₅ | 102 |
| 22. | Cl | CH₂Cl | C₂H₅ | C₆H₅ | 84-85 |
| 23. | Cl | C₂H₅ | C₂H₅ | C₆H₅ | 74-77 |
| 24. | Br | CH₂Cl | CH₃ | C₆H₅ | 80 |
| 25. | Cl | CH₂Cl | CH₃ | C₆H₅ | 91-93 |

The influence of various representatives of the new compounds on the growth of plants is demonstrated in the following experiments.

1. Greenhouse experiments

The vessels employed were plastic flowerpots having a volume of 300 cm³, and which were filled with a sandy loam containing about 1.5% humus. The seeds of the test plants (cf. Table 1) were sown shallow, and separately, according to species. In the case of Cyperus esculentus, pregerminated tubers were used. For the preemergence treatment, the active ingredients were applied to the surface of the soil immediately after the seeds had been shown. The compounds were emulsified or suspended in water as vehicle, and sprayed through finely distributing nozzles. After the agents had been applied, the vessels were lightly sprinkler-irrigated to induce germination and growth and to active the chemical agents. Transparent plastic covers were then placed on the vessels until the plants had taken root. The cover ensured uniform germination of the plants, insofar as this was not impaired by the chemicals.

For postemergence treatment, the plants were first grown to a height of 3 to 10 cm, depending on the growth shape, before being treated. The vessels were not covered after treatment. The pots were set up in the greenhouse-species from warmer areas at from 25° to 40° C., and species from moderate climates at 15° to 30° C. The experiments were run for from 4 to 6 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

2. Experiments in the open

The experiments were carried out on small plots with loamy sand and loam (pH 5 to 6), the humus content being from 1 to 1.5%. In the preemergence treatment, the compounds were applied either immediately after the crop plants had been sown or up to 3 days thereafter. The crop plants were sown in rows. The weed flora was made up of a wide variety of species, and was natural. The substances were emulsified or dispersed in water as vehicle, and applied by means of a motor-driven plot spray mounted on a hitch. Where no rain fell, artifical irrigation was carried out to ensure germination and growth of the crop plants and weeds. All the experiments were run for several months. During this period, assessment on the 0 to 100 scale were made at certain intervals.

Results

Tables 2, 3 and 4 show the results obtained with the new compounds on grassy and broadleaved unwanted plants. Surgarbeets and sunflowers proved to be crop plants which are not damaged by the active ingredient.

The herbicidal action of the new compounds is so strong that, at higher dosage rates, they completely destroy all herbaceous growth. Possible application areas here are the removal of unwanted plant growth under bushes and trees, and on pathways, squares, playgrounds, etc., and in industrial units and on railroad track.

The tables contain the results obtained on pre- and postemergence treatment. Apart from surface application, the agents may of course also be incorporated into the soil, either before or after sowing, or among already established crop plants. Application techniques may, however, also be used in which the agents are sprayed from suitable spray equipment in such a manner that the leaves of the sensitive crop plants are if possible avoided, and reach the soil surface or unwanted plants growing beneath the crop plants (post-directed, lay-by treatment).

TABLE 1

| | List of plant names | |
|---|---|---|
| Botanical name | Abbreviation in tables | Common name |
| Alopecurus myosuroides | Alopec. myos. | slender foxtail |
| Beta vulgaris spp. alt. | Sugarbeets | sugarbeets |
| Chenopodium album | Chenop. album | lambsquarters (goosefoot) |
| Cyperus difformis | Cyper. diff. | smallflower umbrellaplant |
| Cyperus ferax | Cyper. ferax | |
| Datura stramonium | Dat. stram. | Jimsonweed |
| Digitaria sanguinalis | Digita. sang. | large crabgrass |
| Echinochloa crus galli | Echino. c.g. | barnyardgrass |
| Euphorbia geniculata | Euphorb. genic. | South American member of the spurge family |
| Helianthus annuus | Helianth. ann. | sunflowers |
| Matricaria/Anthemis spp. | Matric./Anthem. spp. | chamomile |
| Mercurialis annua | Mercur. annua | annual mercury |
| Polygonum spp. | Polygon. spp. | |
| Sesbania exaltata | Sesbania exalt. | hemp sesbania (coffeeweed) |
| Sinapis alba | Sinapis alba | white mustard |
| Sinapis arvensis | Sinapis arv. | yellow charlock |
| Solanum nigrum | Solanum nigrum | black nightshade |
| Stellaria media | Stellaria media | chickweed |

TABLE 2

Selective herbicidal action of pyridazone derivatives; preemergence application in the open

| Compound no. | kg/ha | Sugar-beets | Alopec. myos. | Chenop. album | Matric./ Anthem.spp. | Polygon spp. | Sinapis arv. | Stellaria media |
|---|---|---|---|---|---|---|---|---|
| 1-phenyl-4-dimethyl-amino-5-chloropyridazone-(6) prior art | 1.5 | 0 | 8 | 7 | 20 | 0 | 8 | 7 |
|  | 2.0 | — | 29 | — | 28 | — | — | 10 |
| 1-phenyl-4-dimethyl-amino-5-bromopyridazone-(6) prior art | 1.5 | — | 10 | 10 | 5 | 0 | 15 | 15 |
| 1-phenyl-4-diethylamino-5-chloropyridazone-(6) prior art | 1.5 | 0 | 5 | 7 | 7 | 2 | 5 | 7 |
| 1-phenyl-4-diethylamino-5-bromopyridazone-(6) | 1.5 | 0 | 15 | 20 | 5 | 0 | 10 | 10 |
| 13 | 1.5 | 0 | — | 48 | 80 | — | — | — |
|  | 2.0 | 0 | 63 | 90 | 77 | 88 | 84 | 97 |
| 14 | 1.5 | 2 | 40 | 97 | 100 | 55 | 53 | 80 |
|  | 2.0 | 6 | 71 | 92 | 100 | 82 | 84 | 82 |
| 15 | 1.5 | 6 | 49 | 81 | 100 | 85 | 55 | 93 |
|  | 2.0 | 13 | 73 | 91 | 100 | 94 | 92 | 99 |
| 16 | 1.0 | 0 | 70 | 70 | — | — | 100 | 90 |
|  | 2.0 | 0 | 95 | 98 | 78 | — | 100 | 87 |
| 17 | 1.5 | 0 | 56 | 72 | 98 | 70 | — | 64 |
|  | 2.0 | 0 | 72 | 86 | 99 | 84 | 80 | 80 |
| 18 | 1.0 | 0 | — | 51 | 90 | 52 | 26 | 23 |
|  | 2.0 | 0.4 | — | 78 | 98 | 66 | 51 | 53 |
| 19 | 1.5 | 0 | 54 | 94 | 100 | 93 | — | 82 |
|  | 2.0 | 4 | 74 | 98 | 100 | 95 | — | 92 |

0 = no damage,
100 = nonemergence, or plants withered

TABLE 3

Selective herbicidal action of pyridazone derivatives; preemergence treatment in the greenhouse

| Compound no. | kg/ha | Helianth. ann. | Cyper. ferax | Digita. sang. | Echino. c.g. | Euphorb. genic. | Sesbania exalt. | Sinapis alba | Solanum nigrum | Stellaria media |
|---|---|---|---|---|---|---|---|---|---|---|
| 10 | 1.0 | 0 | 90 | 100 | 100 | 45 | 98 | 60 | 98 | 30 |
|  | 2.0 | 8 | 90 | 100 | 100 | 100 | 100 | 100 | 100 | 100 |
| 6 | 1.0 | 10 | 100 | 100 | 75 | 100 | 98 | 100 | 100 | 100 |
|  | 2.0 | 15 | 100 | 100 | 80 | 100 | 100 | — | 100 | 100 |
| 12 | 1.0 | 0 | 100 | 40 | 40 | 40 | 100 | 100 | 100 | 100 |
|  | 2.0 | 5 | 100 | 80 | 70 | 100 | 100 | 100 | 100 | 100 |
| 2 | 1.0 | 10 | 95 | 95 | 100 | 100 | 100 | 100 | 100 | 100 |
|  | 2.0 | 18 | 95 | 95 | 100 | 100 | 100 | 100 | 100 | 100 |
| 3 | 1.0 | 0 | 100 | 60 | 100 | 80 | — | 98 | 65 | 100 |
|  | 2.0 | 0 | 100 | 100 | 100 | 100 | — | 98 | 97 | 100 |
| 4 | 1.0 | 0 | 100 | 100 | 70 | 100 | 98 | 100 | 100 | 100 |
|  | 2.0 | 0 | 100 | 100 | 100 | 100 | 100 | 100 | 100 | 100 |
| 11 | 1.0 | 5 | 95 | — | 40 | 40 | 98 | 80 | 70 | — |
|  | 2.0 | 5 | 95 | 90 | 60 | 100 | 100 | 100 | 75 | 100 |
| 1 | 1.0 | 2.5 | 100 | 100 | 100 | 70 | 100 | — | 90 | — |
|  | 2.0 | 2.5 | 100 | 100 | 100 | 100 | 100 | 100 | 100 | 100 |
| 9 | 1.0 | — | 90 | 80 | 90 | — | 80 | 70 | 72 | — |
|  | 2.0 | — | 95 | 100 | 100 | — | 100 | 70 | 99 | 100 |
| 5 | 1.0 | 5 | 95 | 100 | — | 100 | 85 | 100 | 95 | 100 |
|  | 2.0 | 15 | 95 | 100 | 100 | 100 | 100 | 100 | 100 | 100 |

0 = no damage,
100 = nonemergence, or plants withered

TABLE 4

Selective herbicidal action of further compounds; postemergence treatment in the greenhouse

| Compound no. | kg/ha | Helianth. ann. | Cyper. diff. | Dat. stram. | Digit. sang. | Echino. c.g. | Mercur. annua | Sinapis alba | Solanum nigrum | Stellaria media |
|---|---|---|---|---|---|---|---|---|---|---|
| 6 | 0.5 | 0 | 60 | 100 | — | 95 | 80 | 100 | 100 | 100 |
|  | 1.5 | 10 | 80 | 100 | 100 | 98 | 100 | 100 | 100 | 100 |
| 3 | 0.5 | 0 | 92 | 100 | 60 | 80 | 80 | 100 | 75 | 68 |
|  | 1.0 | 0 | 92 | 100 | 80 | 93 | 80 | 100 | 100 | 100 |
| 2 | 0.5 | 0 | 95 | 100 | 100 | 98 | 100 | 100 | 85 | 100 |

TABLE 4-continued

Selective herbicidal action of further compounds; postemergence treatment in the greenhouse

| Compound no. | kg/ha | Helianth. ann. | Cyper. diff. | Dat. stram. | Digit sang. | Echino. c.g. | Mercur. annua | Sinapis alba | Solanum nigrum | Stellaria media |
|---|---|---|---|---|---|---|---|---|---|---|
| | 1.0 | 8 | 95 | 100 | 100 | 100 | 100 | 100 | 100 | 100 |

In view of the many application methods possible, the agents according to the invention, or mixtures containing them, may be used not only on the crop plants listed in the tables, but also in a much larger range of crops for removing unwanted plants. Depending on the object to be achieved, the application rates vary from 0.1 to 15 kg/ha and more.

The following crop plants may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapas var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Gylcine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus pp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (S. vulgare) | grain sorghum |
| Sorghum dochna | |
| Spinacia oleracea | spinach |
| Theobroma cacao | cacao plants |
| Trifolium pratense | red clover |
| Triticum asetivum | wheat |
| Vaccinium corymbosum | blueberries |
| Vaccinium vitis-idaea | cranberries |
| Vicia faba | tick beans |
| Vigna sinensis (V. ungulculata) | cow peas |
| Vitis vinifera | grapes |
| Zea mays | Indian corn, sweet corn, maize |

The new pyridazones may be mixed and applied together with numerous representatives of other herbicidal or growth-regulating active ingredient groups. These combinations extend the spectrum of action, and synergistic effects are achied with some of them. Examples of active ingredients giving, with the new compounds, useful mixtures for a wide variety of applications are given below:

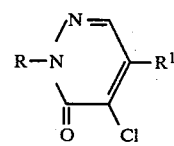

R          R¹

-continued
| | | |
|---|---|---|
| 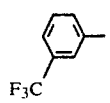 | —NHCH₃ | |
| 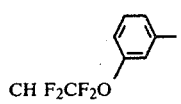 | —NH—CH₃ | |
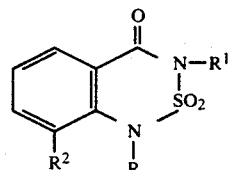
| R | R¹ | R² | |
|---|---|---|---|
| H | ⫽ (isopropyl) | H | and salts |
| H | ⫽ | Cl | " |
| H | ⫽ | F | " |
| H | ⫽ | CH₃ | " |
| CH₂OCH₃ | ⫽ | H | " |
| CH₂OCH₃ | ⫽ | F | " |
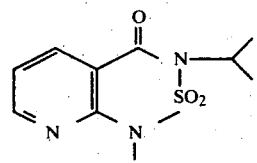
"
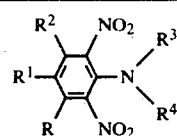
| R | R¹ | R² | R³ | R⁴ |
|---|---|---|---|---|
| H | H₃CSO₂ | H | n-C₃H₇ | n-C₃H₇ |
| H | F₃C | H | C₂H₅ | C₄H₉ |
| H | F₃C | H | n-C₃H₇ | n-C₃H₇ |
| H | F₃C | H | —CH₂—CH₂Cl | n-C₃H₇ |
| H | SO₂NH₂ | H | n-C₃H₇ | n-C₃H₇ |
| H | F₃C | H | n-C₃H₇ | —CH₂—◁ |
| H₃C | H₃C | H | H | —CH(C₂H₅)(C₂H₅) |
| H | F₃C | NH₂ | n-C₃H₇ | n-C₃H₇ |
| H | H₃C | H | n-C₃H₇ | n-C₃H₇ |
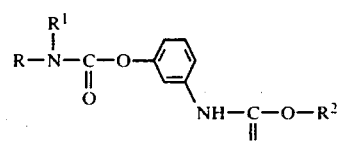
| R | R¹ | R² |
|---|---|---|

-continued

| R | R¹ | R² |
|---|---|---|
| 3-methylphenyl (H₃C-C₆H₄-) | H | CH₃ |
| phenyl | H | C₂H₅ |
| phenyl | CH₃ | CH₃ |
| 4-fluorophenyl | H | CH₃ |

$$R-\underset{\underset{O}{\|}}{N}(R^1)-C-O-C_6H_4-NH-\underset{\underset{O}{\|}}{C}-O-R^2$$

| R | R¹ | R² |
|---|---|---|
| 3,4-difluorophenyl | H | C₂H₅ |
| 3-chloro-4-fluorophenyl | H | C₂H₅ |

$$R^1-O-\underset{R^2}{\overset{}{C}}H-\underset{\underset{O}{\|}}{C}-O-R^3$$

| R | R² | R³ |
|---|---|---|
| 2,4-dichlorophenyl | H | H — salts, esters, amides |
| 2,4-dichlorophenyl | CH₃ | H — salts, esters, amides |
| 4-chloro-2-methylphenyl | H | H — salts, esters, amides |
| 4-chloro-2-methylphenyl | CH₃ | H — salts, esters, amides |

| R | R² | R³ |
|---|---|---|
| 2,4,5-trichlorophenyl | H | H — salts, esters, amides |
| 2,4,5-trichlorophenyl | CH₃ | H — salts, esters, amides |

$$\underset{R}{\overset{R^1}{N}}-\underset{\underset{O}{\|}}{C}-S-R^2$$

| R | R¹ | R² |
|---|---|---|
| i-C₃H₇ | i-C₃H₇ | -CH₂-(3-methyl-isoxazol-5-yl) |

-continued

| | | |
|---|---|---|
| i-C$_3$H$_7$ | i-C$_3$H$_7$ | -CH$_2$-[3-ethyl-isoxazol-5-yl] |

$$\begin{array}{c} R^1 \\ | \\ R-N-C(=O)-S-R^2 \end{array}$$

| R | R$^1$ | R$^2$ |
|---|---|---|
| n-C$_3$H$_7$ | n-C$_3$H$_7$ | C$_2$H$_5$ |
| cyclohexyl-CH | C$_2$H$_5$ | C$_2$H$_5$ |
| sec.C$_4$H$_9$ | sec.C$_4$H$_9$ | C$_2$H$_5$ |
| n-C$_3$H$_7$ | n-C$_3$H$_7$ | n-C$_3$H$_7$ |

| R | R$^1$ | R$^2$ |
|---|---|---|
| C$_2$H$_5$ | C$_2$H$_5$ | -CH$_2$-C$_6$H$_4$-Cl |
| norbornyl | C$_2$H$_5$ | C$_2$H$_5$ |
| i-C$_3$H$_7$ | i-C$_3$H$_7$ | CH$_2$-CCl=CHCl |
| n-C$_3$H$_7$ | n-C$_3$H$_7$ | C$_2$H$_5$ |

$$\text{hexamethyleneimino-}C(=O)-S-C_2H_5$$

$$\begin{array}{c} X \\ | \\ R-C-C(=O)-O-R^1 \\ | \\ Y \end{array}$$

| R | X | Y | R$^1$ |
|---|---|---|---|
| CH$_3$ | Cl | Cl | Na |
| | Cl | H | CH$_3$ |
| 4-Cl-C$_6$H$_4$-CH$_2$- | | | |
| | H | H | H |
| C$_6$H$_5$-C(=O)-HNO- | | | |
| Cl | Cl | Cl | Na |
| | H | CH$_3$ | CH$_3$ |
| 2,4-Cl$_2$-C$_6$H$_3$-O-C$_6$H$_4$-O- | | | |
| | H | CH$_3$ | C$_2$H$_5$ |
| C$_6$H$_5$-C(=O)-N(3,4-Cl$_2$-C$_6$H$_3$)- | | | |

$$\begin{array}{c} X \\ | \\ R-C-C(=O)-O-R^1 \\ | \\ Y \end{array}$$

| R | X | Y | R$^1$ |
|---|---|---|---|
| C$_6$H$_5$-C(=O)-N(3-Cl-4-F-C$_6$H$_3$)- | H | CH$_3$ | i-C$_3$H$_7$ |
| 4-Cl-C$_6$H$_4$-O-C$_6$H$_4$-O- | O | CH$_3$ | -CH$_2$-CH(CH$_3$)$_2$ |

-continued

| Structure | | | | |
|---|---|---|---|---|
| 3-Cl, 5-Cl pyridyl-2-oxy-(4-methoxyphenoxy) | H | CH₃ | Na | |
| 2-Cl, 4-CF₃-phenoxy-(4-methoxyphenoxy) | H | CH₃ | Na | |
| 4-CF₃-phenoxy-(4-methoxyphenoxy) | H | CH₃ | CH₃ | |

$$\begin{array}{c} X \\ \| \\ R^1\diagdown N \diagup \diagdown N \diagup R^2 \\ R \diagup N \diagdown \diagup N \diagdown R^3 \end{array}$$

| R | R¹ | X | R² | R³ |
|---|---|---|---|---|
| H | C₂H₅ | SCH₃ | H | C₂H₅ |
| H | i-C₃H₇ | SCH₃ | H | C₂H₅ |
| H | CH₃ | SCH₃ | H | i-C₃H₇ |
| H | i-C₃H₇ | Cl | H | C₂H₅ |

| R | R¹ | X | R² | R³ |
|---|---|---|---|---|
| H | i-C₃H₇ | Cl | H | cyclopropyl |
| H | C₂H₅ | Cl | H | C₂H₅ |
| H | C₂H₅ | Cl | H | —C(CH₃)₂—CN |
| H | C₂H₅ | OCH₃ | H | C₂H₅ |
| H | i-C₃H₇ | OCH₃ | H | i-C₃H₇ |
| H | C₂H₅ | Cl | H | —CH(CH₃)—CH₂·OCH₃ |
| H | C₂H₅ | Cl | H | —CH(CH₃)—C≡CH |

$$\begin{array}{c} R^1 \\ \diagdown N-C-R^2 \\ R \diagup \| \\ O \end{array}$$

| R | R¹ | R² |
|---|---|---|
| CH₃ | CH₃ | —CH(C₆H₅)₂ |
| 1-naphthyl | H | 2-COOH-phenyl |
| 3,4-dichlorophenyl | H | cyclopropyl |
| 3,4-dichlorophenyl | H | C₂H₅ |

| R | R¹ | R² |
|---|---|---|
| 4-chlorophenyl | H | —C(CH₃)₂—CH₂—CH₂—CH₃ |
| phenyl | —CH(CH₃)—C≡CH | CH₂Cl |
| 2-CH₃, 6-C₂H₅-phenyl | —CH(CH₃)—CH₂—OCH₃ | CH₂Cl |

-continued

| | $-CH_2-OCH_3$ | $CH_2Cl$ |
|---|---|---|
| 2,6-diethylphenyl | | |
| 2,6-diethylphenyl | $-CH_2-\underset{\underset{O}{\|}}{C}-OC_2H_5$ | $CH_2Cl$ |
| 2,6-diethylphenyl | $i\text{-}C_3H_7$ | $CH_2Cl$ |
| phenyl | | |
| 2,6-diethylphenyl | $-CH_2-O-C_4H_9\text{-}n.$ | $CH_2Cl$ |
| 2,6-dimethylphenyl | $-CH_2-\underset{\text{1,3-dioxolan-2-yl}}{} $ | $CH_2Cl$ |
| 3,5-dimethylphenyl | $-CH_2-CH_2-OCH_3$ | $CH_2Cl$ |

$$R^1\underset{R}{N}-\underset{\underset{O}{\|}}{C}-R^2$$

| R | $R^1$ | $R^2$ |
|---|---|---|
| $C_2H_5$ | $C_2H_5$ | $-\underset{\underset{CH_3}{\|}}{CH}-O-\text{naphthyl}$ |
| $CH_2=CH-CH_2-$ | $CH_2=CH-CH_2-$ | $CH_2Cl$ |
| $HC{\equiv}C-\underset{\underset{CH_3}{\|}}{\overset{\overset{CH_3}{\|}}{C}}-$ | H | 3,5-dichlorophenyl |
| 2-methyl-5-(F_3CSO_2NH)-phenyl | H | $CH_3$ |
| 2,4-dimethyl-5-(F_3CSO_2NH)-phenyl | H | $CH_3$ |

4-OR-3,5-XY-benzonitrile

| X | Y | R |
|---|---|---|
| Br | Br | H (salts) |
| I | I | H (salts) |
| Br | Br | $-\underset{\underset{O}{\|}}{C}-(CH_2)_6-CH_3$ salts, esters |

$$O_2N\text{-}(2,4\text{-dinitrophenyl})-O-N{=}CH-(3,5\text{-dibromo-4-hydroxyphenyl})$$

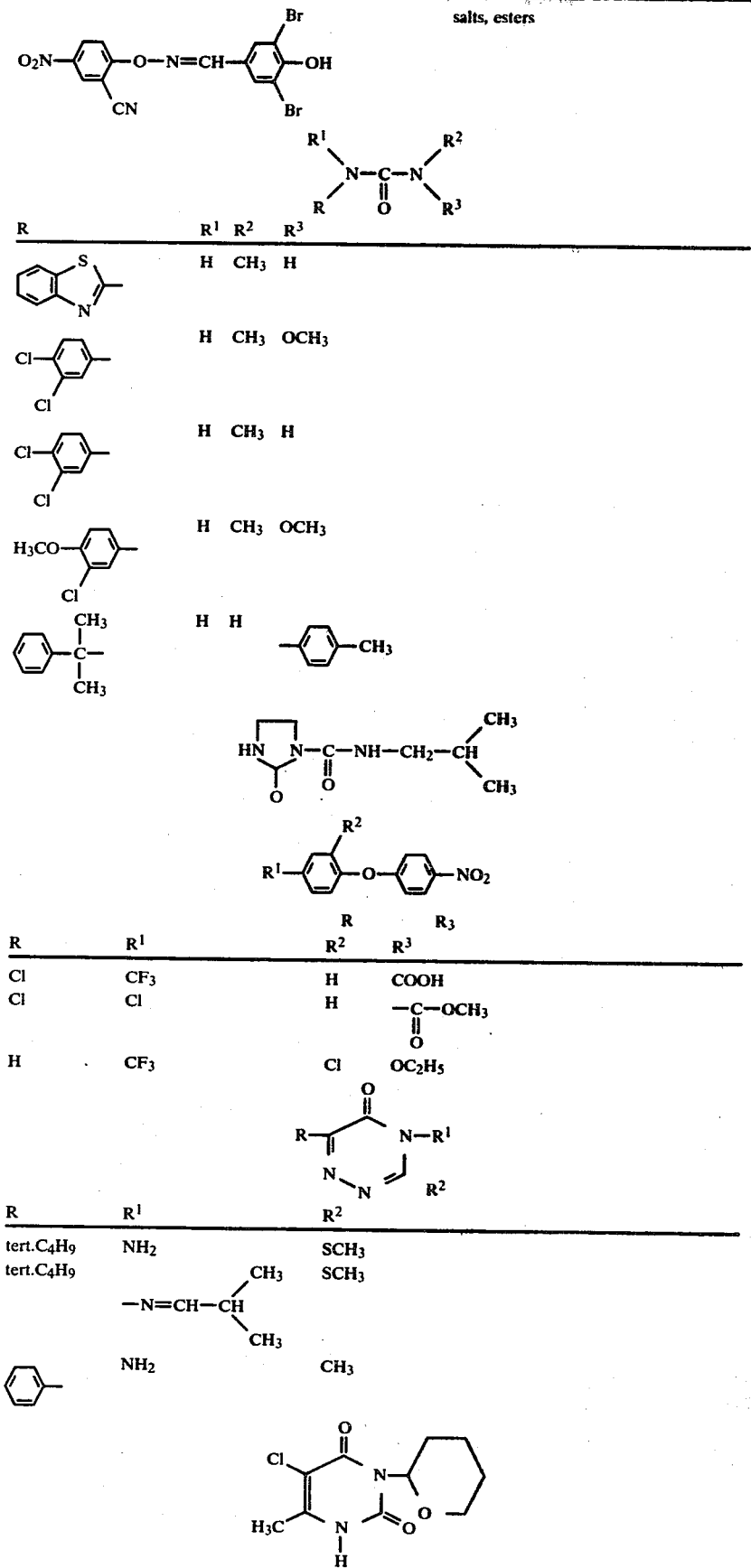

-continued
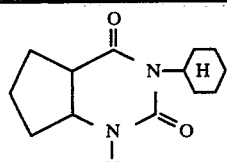
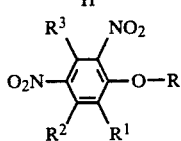
| R | R$^1$ | R$^2$ | R$^3$ |
|---|---|---|---|
| —C(=O)—CH$_3$ | sec.C$_4$H$_9$ | H | H |
| H | CH$_3$ | H | H (salts, esters) |
| H | sec.C$_4$H$_9$ | H | H (salts, esters) |
| —C(=O)—CH$_3$ | tert.C$_4$H$_9$ | H | H |
| —C(=O)—CH$_3$ | tert.C$_4$H$_9$ | H | CH$_3$ |
| H | tert.C$_4$H$_9$ | H | H (salts, esters) |
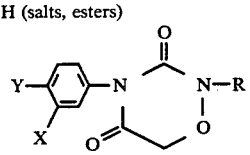
| X | Y | R |
|---|---|---|
| CF$_3$ | H | CH$_3$ |
| H | F | CH$_3$ |
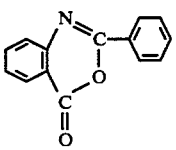
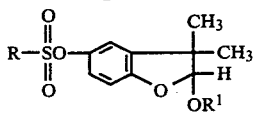
| R | R$^1$ |
|---|---|
| CH$_3$ | C$_2$H$_5$ |
| (H$_3$C)$_2$N— | C$_2$H$_5$ |
| H$_3$C−N(CH$_3$)−C(=O)−CH$_3$ | C$_2$H$_5$ |
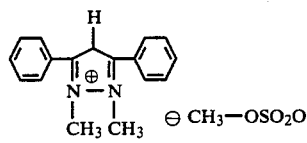
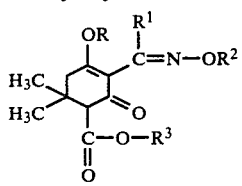
| R | R$^1$ | R$^2$ | R$^3$ |
|---|---|---|---|
| H | n-C$_3$H$_7$ | —CH$_2$—CH=CH$_2$ | CH$_3$ |
| Na | n-C$_3$H$_7$ | —CH$_2$—CH=CH$_2$ | CH$_3$ |

-continued
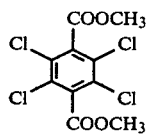
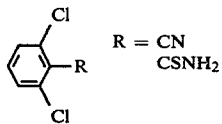
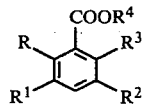
| R | R$^1$ | R$^2$ | R$^3$ | R$^4$ |
|---|---|---|---|---|
| H | Cl | NH$_2$ | Cl | H (salts, esters, amides) |
| Cl | Cl | H | Cl | H (salts, esters, amides) |
| H | I | I | I | H (salts, esters, amides) |
| Cl | H | Cl | OCH$_3$ | H (salts, esters, amides) |
| | | | | (salts, esters, amides) |
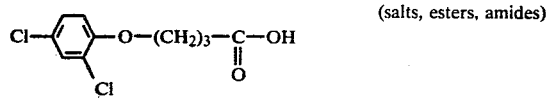
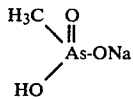
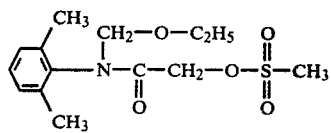
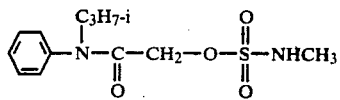
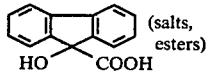 (salts, esters)
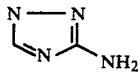
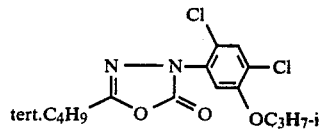
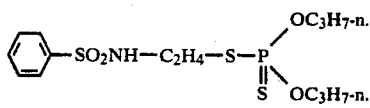
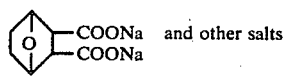 and other salts -continued
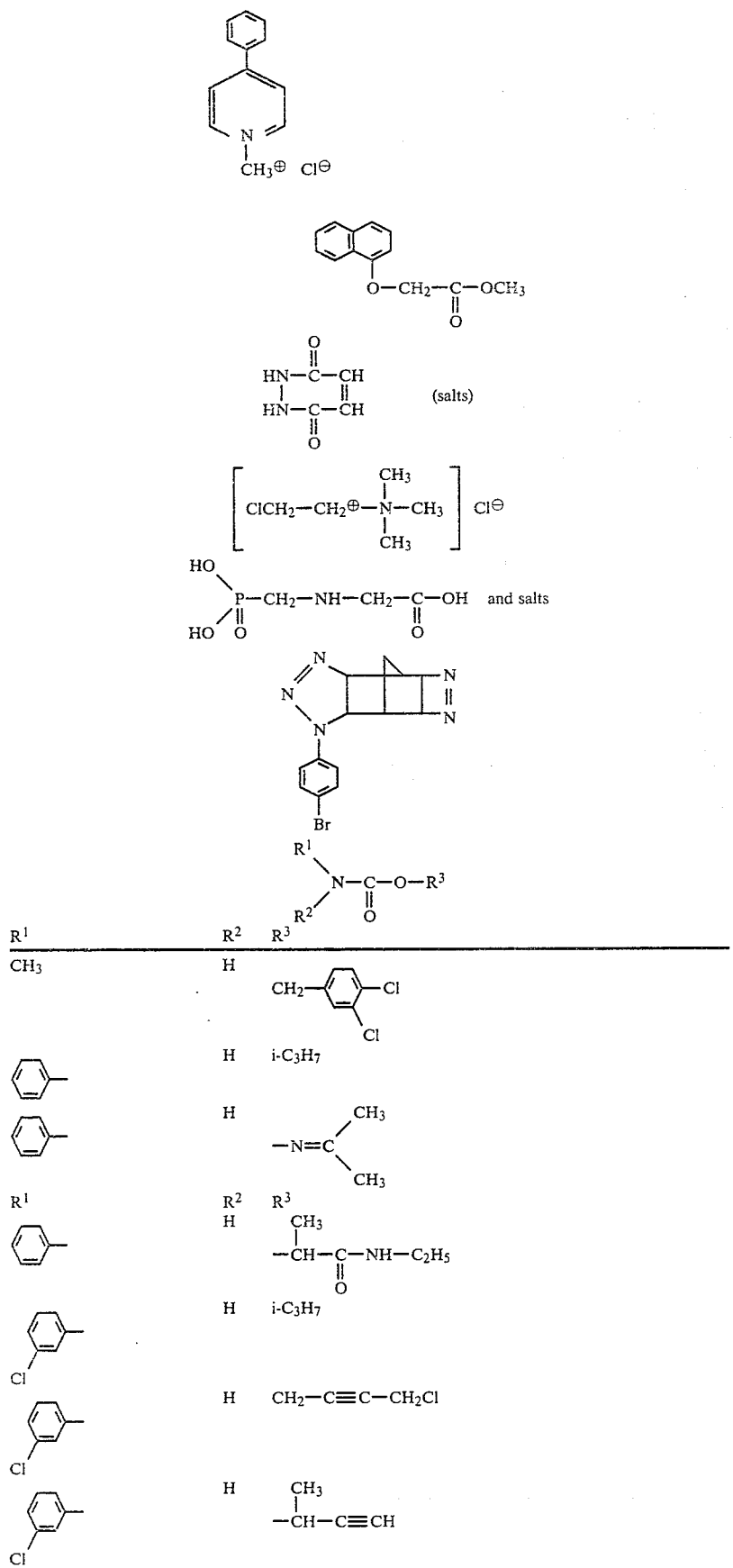

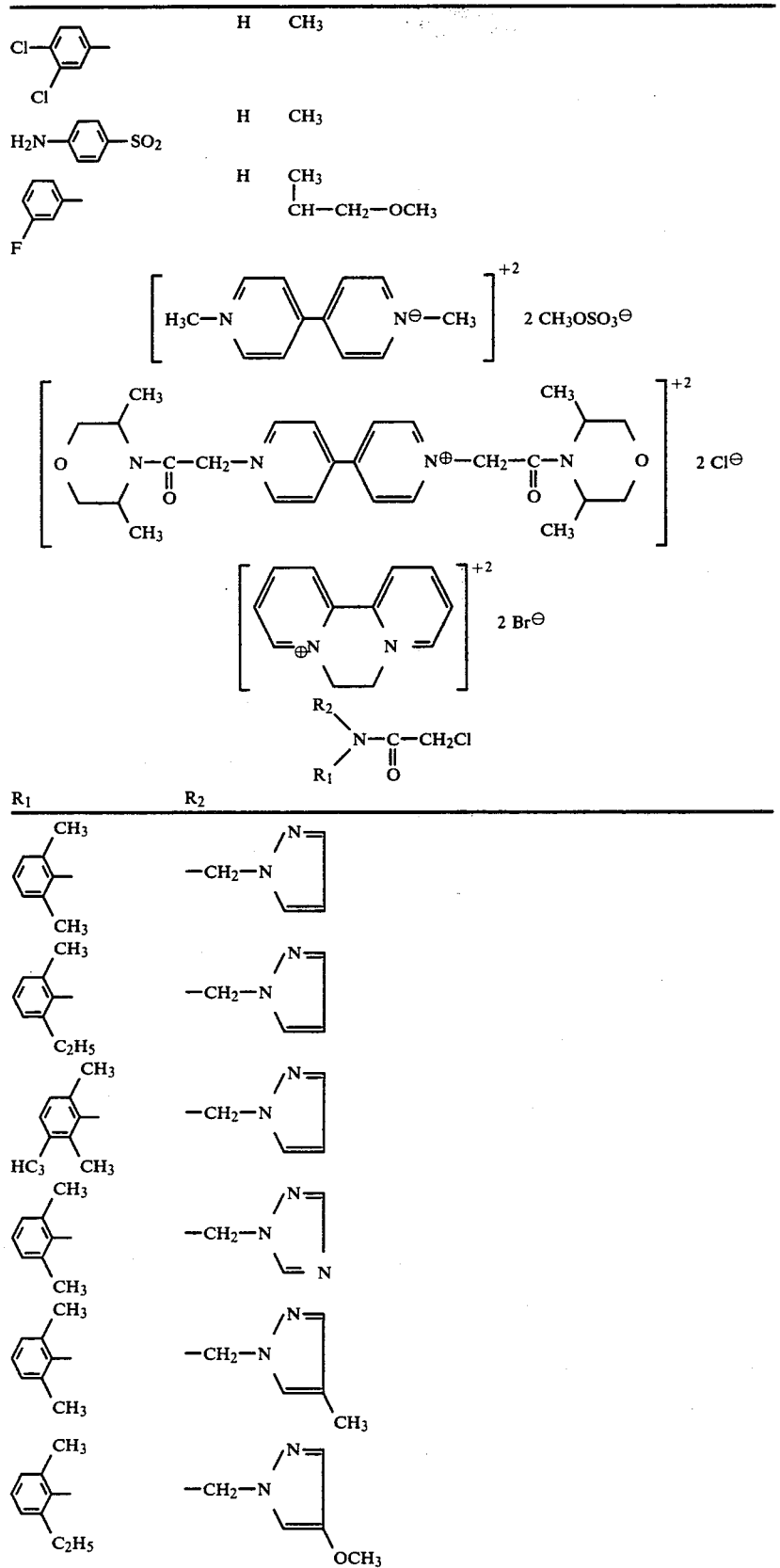
It may also be useful to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies, and with mineral fertilizers containing nitrogen, phosphate or potassium.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depent entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. Application rates are from 0.1 to 10 kg of active ingredient per hectare.

There may be added to the compositions or individual active ingredients oils of various types, wetting agents or adherents, herbicides, fungicides, nematocides, insecticides, bactericides, trace elements, fertilizers, antifoams (e.g., silicones), growth regulators, antidotes and other herbicidally effective compounds. These agents may be added to the herbicides according to the invention in a weight ratio of from 1:10 to 10:1.

EXAMPLE 2

90 parts by weight of compound 1 is mixed with 10 parts by weight of N-methyl-α-pyrrolidone. A mixture is obtained which is suitable for application in the form of very fine drops.

EXAMPLE 3

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 4

20 parts by weight of compound 2 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 5

20 parts by weight of compound 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 7

3 parts by weight of compound 1 is intimately mixed with 97 parts by weight of particulate kaolin. A dust is obtained containing 3% by weight of the active ingredient.

EXAMPLE 8

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 9

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 10

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A pyridaz-6-one compound of the formula

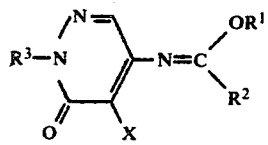

where X denotes halogen, $R^1$ denotes $C_1$-$C_6$-alkyl, $R^2$ denotes H, $C_1$-$C_6$-alkyl or haloalkyl, and $R^3$ denotes phenyl or cyclohexyl.

2. A process for combating unwanted plant growth, wherein the plants or the soil are treated with a herbicidally effective amount of a composition containing from 0.1 to 95% by weight of a compound of the formula

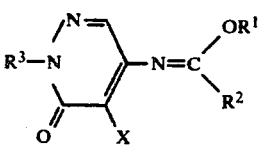

where X denotes halogen, $R^1$ denotes $C_1$-$C_6$-alkyl, $R^2$ denotes H, $C_1$-$C_6$-alkyl or haloalkyl, and $R^3$ denotes phenyl or cyclohexyl.

3. A compound selected from the group consisting of

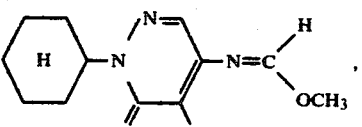

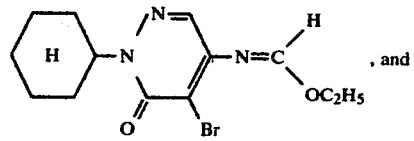, and

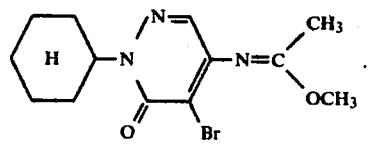

* * * * *